(12) United States Patent
Shibata et al.

(10) Patent No.: US 9,000,156 B2
(45) Date of Patent: Apr. 7, 2015

(54) PROCESS FOR PRODUCING SUBSTITUTED METHYLAMINE COMPOUND AND TRIAZINE DERIVATIVE

(75) Inventors: Yasushi Shibata, Odawara (JP); Tsutomu Imagawa, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 408 days.

(21) Appl. No.: 12/596,950

(22) PCT Filed: Apr. 24, 2007

(86) PCT No.: PCT/JP2007/058842
§ 371 (c)(1),
(2), (4) Date: Oct. 21, 2009

(87) PCT Pub. No.: WO2008/136093
PCT Pub. Date: Nov. 13, 2008

(65) Prior Publication Data
US 2010/0121054 A1 May 13, 2010

(51) Int. Cl.
C07D 401/06 (2006.01)
C07D 401/14 (2006.01)
C07D 213/61 (2006.01)
C07D 257/08 (2006.01)
C07D 277/20 (2006.01)
C07D 307/04 (2006.01)
C07D 319/14 (2006.01)
C07D 339/08 (2006.01)
C07C 211/03 (2006.01)
C07C 211/48 (2006.01)
C07C 211/62 (2006.01)
C07C 209/06 (2006.01)
C07B 43/04 (2006.01)

(52) U.S. Cl.
CPC ............ C07D 213/61 (2013.01); C07C 211/48 (2013.01); C07D 277/20 (2013.01); C07D 257/08 (2013.01); C07C 211/03 (2013.01); C07C 211/62 (2013.01); C07C 209/06 (2013.01); C07B 43/04 (2013.01); C07D 401/06 (2013.01); C07D 401/14 (2013.01)

(58) Field of Classification Search
CPC .............. C07D 401/06; C07D 213/61; C07D 251/047; C07D 257/08; C07D 257/047; C07D 277/20; C07C 209/06; C07C 211/03; C07C 211/48; C07C 211/62
USPC ........................................................ 544/185
See application file for complete search history.

(56) References Cited

U.S. PATENT DOCUMENTS 1,471,213 A 10/1923 Shepard et al.
4,002,564 A 1/1977 Carbonel et al.
6,627,228 B1 9/2003 Milstein et al.

8,269,044 B2 * 9/2012 Takano et al. ................. 564/386
2004/0122057 A1 6/2004 Banner et al.
2009/0281325 A1 * 11/2009 Takano et al. ................. 546/329

FOREIGN PATENT DOCUMENTS

DE 3727 126 2/1989
DE 19843383 3/2000
EP 1961733 A1 8/2008
JP 63-027465 2/1988
JP 03-271273 12/1991

(Continued)

OTHER PUBLICATIONS

English Translation of JP 08-295670, Dec. 11, 1996.*

(Continued)

*Primary Examiner* — Venkataraman Balasubramanian
(74) *Attorney, Agent, or Firm* — Kenyon & Kenyon, LLP

(57) ABSTRACT

The present invention provides a process that enables a substituted methylamine compound which is useful as an intermediate for the production of agricultural chemicals and medicines, to be produced easily, with good yield, and at low cost, and also provides a production intermediate thereof. The process comprises a step of reacting a hexamethylenetetraammonium salt compound represented by a formula (I) with a base to obtain an N-methylidene-substituted methylamine oligomer represented by a formula (II) or a mixture of two or more of the oligomers, and a step of hydrolyzing the N-methylidene-substituted methylamine oligomer represented by formula (II) or the mixture of two or more of the oligomers in the presence of an acid.

[Chemical Formula 1]

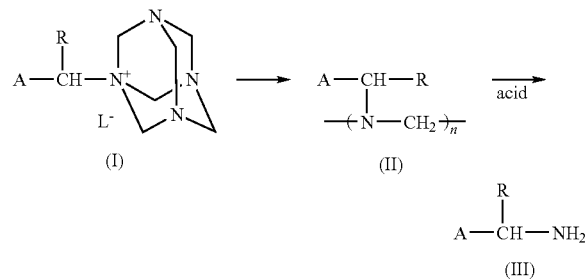

(wherein A represents an organic group that is either a hydrocarbon group or a heterocyclic group, or said organic group that has a substituent, R represents a hydrogen atom, an organic group that is either a hydrocarbon group or a heterocyclic group, or said organic group that has a substituent, L represents a halogen atom and the like, and n represents an integer of 2 to 20)

11 Claims, No Drawings

(56) References Cited

FOREIGN PATENT DOCUMENTS

| JP | 5-230026 | 9/1993 |
|----|----------|--------|
| JP | 08-295670 | 11/1996 |
| JP | 10-045683 | 2/1998 |
| WO | WO-2006/109811 A1 | 10/2006 |
| WO | 2007/069685 A1 | 6/2007 |
| WO | WO 2007069685 A1 * | 6/2007 |

OTHER PUBLICATIONS

English Translation of JP 05-230026, Jul. 9, 1993.*
DE 198433383 Mar. 30, 2000;English Translation of Text.*
"Development of a RH-Intelligent Catalyst," Zh. Prkil, (1975), vol. 48., No. 8, pp. 1802-1805.
Final Office Action issued for U.S. Appl. No. 13/274,469, dated Jun. 26, 2012.
Japanese Office Action issued for JP 2009-512826, dated Jun. 12, 2012, with English translation, 6 pages.
EP Communication including European Search Report from EP Appln. No. 13175480.6, dated Sep. 9, 2013, 5 pages.
European Search Report, mailed Dec. 17, 2010, issued during prosecution of EP Application No. 07742277.2.
Huaifeng Jia et al., "Synthesis of Arylmethyl Amine by Hexamethylenetetramine Based Method", Chinese Journal of Synthetic Chemistry, vol. 13, 2005, No. 6, pp. 630-631.
Japanese Patent Office, International Search Report (translated) mailed Aug. 7, 2007, from related International Patent Application No. PCT/JP2007/058842.

* cited by examiner

US 9,000,156 B2

PROCESS FOR PRODUCING SUBSTITUTED METHYLAMINE COMPOUND AND TRIAZINE DERIVATIVE

TECHNICAL FIELD

The present invention relates to a process that enables a substituted methylamine compound, such as a pyridylmethylamine compound, which is useful as an intermediate for the production of agricultural chemicals and medicines and the like, to be produced easily, with good yield, and at low cost, and also relates to an N-methylidene-substituted methylamine oligomer that acts as a production intermediate.

BACKGROUND ART

Substituted methylamine compounds, including pyridylmethylamine compounds such as 2-chloro-5-pyridylmethylamine, are useful as intermediates for the production of agricultural chemicals and medicines.

Conventionally, known processes for producing pyridylmethylamine compounds include a process in which 2-chloro-5-chloromethylpyridine is reacted with potassium phthalimide to obtain N-(2-chloro-5-pyridylmethyl)phthalimide, which is subsequently reacted with hydrazine (see Patent Document 1), a process in which 2-chloro-5-(chloromethyl) pyridine is reacted with hexamethylenetetramine to obtain 2-chloro-5-pyridylmethylhexamethylenetetraanunonium chloride, and a hydrolysis is subsequently performed in the presence of a lower alcohol and a mineral acid (see Patent Document 2), and a process in which 2-chloro-5-pyridylmethylhexamethylenetetraammonium chloride is hydrolyzed using water or alkaline water to generate N-methylidene-2-chloro-5-pyridylmethylamine, which is subsequently isolated and then hydrolyzed in an acid (see Patent Document 3).

However, none of these production processes can be claimed to be entirely satisfactory from an industrial perspective. Namely, the first process requires the use of the comparatively expensive potassium phthalimide as a raw material, meaning the process is undesirable from an economic perspective. Further, because an operation is required to remove phthalazine from the hydrazine reaction mixture, the post-processing operation tends to be complex. In the case of the second process, the amount of solvent used in the reaction is large, and a large amount of comparatively expensive hexamethylenetetramine must also be used, and therefore the process is undesirable from an economic perspective. Further, in this process, because the generated 2-chloro-5-pyridylmethylhexamethylenetetraammonium chloride must be first isolated, before being subjected to hydrolysis, a problem arises in that the operation is overly complex. In the third process, a problem arises in that the isolated N-methylidene-2-chloro-5-pyridinemethylamine is unstable and difficult to handle.

[Patent Document 1]
(West) German Pat. No. 3,727,126
[Patent Document 2]
Japanese Unexamined Patent Application, First Publication No. Hei 3-271273
[Patent Document 3]
Japanese Unexamined Patent Application, First Publication No. Hei 8-295670

DISCLOSURE OF THE INVENTION

Problems to be Solved by the Invention

The present invention has been developed in light of the issues associated with the prior arts described above, and has an object of providing a process that enables a substituted methylamine compound, preferably a pyridylmethylamine compound, that is useful as an intermediate for the production of agricultural chemicals and medicines to be produced easily, with good yield, and at low cost, and the production intermediate thereof.

Means to Solve the Problems

As a result of intensive research aimed at achieving the above object, the inventors of the present invention discovered that by reacting a hexamethylenetetraammonium salt compound with a base, an N-methylidene-substituted methylamine oligomer represented by formula (II) below, or a mixture of two or more such oligomers, could be obtained with good yield. Further, the inventors also discovered that by hydrolyzing this mixture in the presence of an acid, a substituted methylamine compound represented by formula (III) below, which represents the target product, could be obtained with good yield, and they were therefore able to complete the present invention.

Accordingly, a first aspect of the present invention provides a process for producing a substituted methylamine compound, the process comprising:

reacting a hexamethylenetetraammonium salt compound represented by formula (I) shown below:

[Chemical Formula 1]

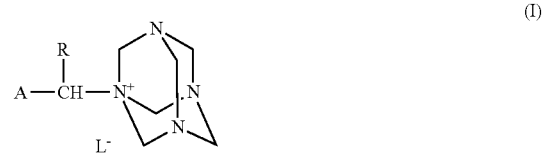

(wherein A represents an organic group that is either a hydrocarbon group or a heterocyclic group, or said organic group that has a substituent, R represents a hydrogen atom, an organic group that is either a hydrocarbon group or a heterocyclic group, or said organic group that has a substituent, and L represents a halogen atom, an alkylsulfonyloxy group of 1 to 20 carbon atoms, a haloalkylsulfonyloxy group of 1 to 20 carbon atoms, or a substituted or unsubstituted arylsulfonyloxy group) with a base to obtain an N-methylidene-substituted methylamine oligomer represented by formula (II) shown below:

[Chemical Formula 2]

(wherein A and R are as defined above, and n represents an integer of 2 to 20), or a mixture of two or more of the oligomers, and hydrolyzing the N-methylidene-substituted methylamine oligomer represented by formula (II) or the mixture of two or more of the oligomers in the presence of an acid, thereby producing a substituted methylamine compound represented by a formula (III) shown below:

[Chemical Formula 3]

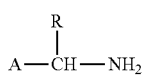

(III)

(wherein A and R are as defined above).

The abovementioned A preferably represents one group selected from the group consisting of organic groups including a phenyl group, a pyridyl group, a thiazolyl group, a dithianyl group and a tetrahydrofuranyl group, and said organic groups having a substituent.

More preferably, A represents one group selected from the group consisting of groups represented by formulas (IV) to (X) shown below:

[Chemical Formula 4]

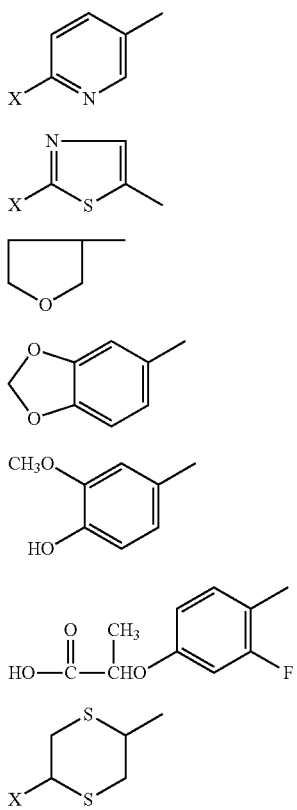

(IV)

(V)

(VI)

(VII)

(VIII)

(IX)

(X)

(wherein X represents a hydrogen atom, a halogen atom, or a substituted or unsubstituted alkyl group).

The group A is still more preferably a 2-chloropyridin-5-yl group.

Furthermore, the abovementioned R preferably represents a hydrogen atom, or a substituted or unsubstituted lower alkyl group, and more preferably represents a hydrogen atom or an alkyl group of 1 to 5 carbon atoms.

In the process for producing a substituted methylamine compound of the present invention, the reaction between the hexamethylenetetraammonium salt compound represented by formula (I) and the base is preferably conducted at a pH of 9 to 12.

A second aspect of the present invention provides a process for producing a substituted methylamine compound, the process comprising:

reacting a substituted methyl compound represented by formula (XI) shown below:

[Chemical Formula 5]

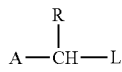

(XI)

(wherein A represents an organic group that is either a hydrocarbon group or a heterocyclic group, or said organic group that has a substituent, R represents a hydrogen atom, an organic group that is either a hydrocarbon group or a heterocyclic group, or said organic group that has a substituent, and L represents a halogen atom, an alkylsulfonyloxy group of 1 to 20 carbon atoms, a haloalkylsulfonyloxy group of 1 to 20 carbon atoms, or a substituted or unsubstituted arylsulfonyloxy group) with hexamethylenetetramine, or ammonia or an ammonium salt and formaldehyde or a formaldehyde equivalent, and a base to obtain an N-methylidene-substituted methylamine oligomer represented by formula (II) shown below:

[Chemical Formula 6]

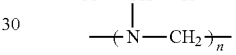

(II)

(wherein A and R are as defined above, and n represents an integer of 2 to 20),
or a mixture of two or more of the oligomers, and hydrolyzing the substituted methylamine oligomer represented by formula (II) or the mixture of two or more of the oligomers in the presence of an acid, thereby producing a substituted methylamine compound represented by a formula (III) shown below:

[Chemical Formula 7]

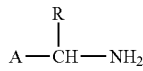

(III)

(wherein A and R are as defined above).

The abovementioned A preferably represents one group selected from the group consisting of organic groups including a phenyl group, a pyridyl group, a thiazolyl group, a dithianyl group and a tetrahydrofuranyl group, and said organic groups having a substituent.

More preferably, A represents one group selected from the group consisting of groups represented by formulas (IV) to (X) shown below:

[Chemical Formula 8]

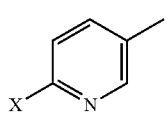

(IV)

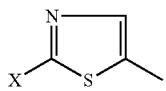
(V)

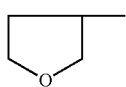
(VI)

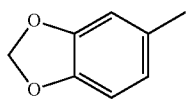
(VII)

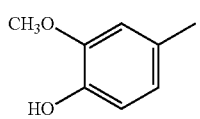
(VIII)

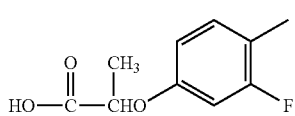
(IX)

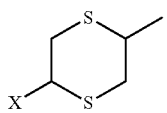
(X)

(wherein X represents a hydrogen atom, a halogen atom, or a substituted or unsubstituted alkyl group).

The group A is still more preferably a 2-chloropyridin-5-yl group.

Furthermore, the abovementioned R preferably represents a hydrogen atom, or a substituted or unsubstituted lower alkyl group, and more preferably represents a hydrogen atom or an alkyl group of 1 to 5 carbon atoms.

In the production process of the present invention, the reaction between the substituted methyl compound represented by formula (XI), the hexamethylenetetramine, or the ammonia or ammonium salt and the formaldehyde or formaldehyde equivalent, and the base is preferably conducted at a pH of 9 to 12.

Further, in the production process of the present invention, it is preferable that the hexamethylenetetramine, or the ammonia and formaldehyde, are recovered from the reaction mixture obtained following the reaction of the substituted methyl compound represented by formula (XI) with the hexamethylenetetramine, or the ammonia or ammonium salt and the formaldehyde or formaldehyde equivalent, and the base, and are subsequently reused in reaction with the substituted methyl compound represented by formula (XI).

A third aspect of the present invention provides an N-methylidene-pyridylmethylamine oligomer represented by formula (II') shown below:

[Chemical Formula 9]

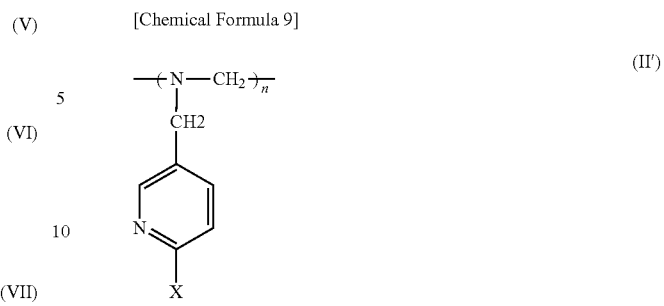
(II')

(wherein X represents a hydrogen atom, a halogen atom, or a substituted or unsubstituted alkyl group, and n represents an integer of 2 to 20).

This oligomer is useful as an intermediate for the production of a substituted methylamine compound represented by formula (III). Of the various oligomers, an N-methylidene-substituted methylamine trimer in which n=3, which is a triazine derivative represented by formula (II") shown below, is preferred.

[Chemical Formula 10]

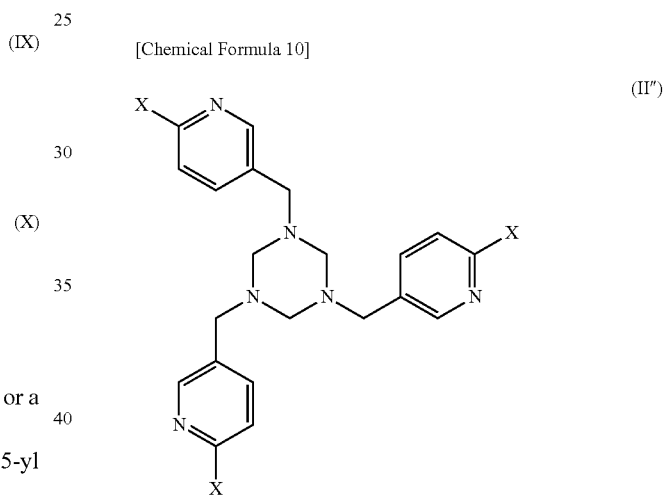
(II")

(wherein X is as defined above.)

Effect of the Invention

According to the present invention, a substituted methylamine compound represented by formula (III) can be produced in an industrially favorable manner, namely, easily, with good yield, and at low cost.

An N-methylidene-substituted methylamine oligomer of the present invention is useful as an intermediate for producing a substituted methylamine compound represented by formula (III).

BEST MODE FOR CARRYING OUT THE INVENTION

A more detailed description of the present invention is presented below.

A process for producing a substituted methylamine compound represented by formula (III) (hereafter also referred to as "the amine compound (III)") comprises a step (hereafter referred to as "step (1)") of reacting a substituted methylhexamethylenetetraammonium salt compound represented by formula (I) shown above (hereafter also referred to as "the ammonium salt compound (I)") with a base to obtain an N-methylidene-substituted methylamine oligomer represented by formula (II) (hereafter also referred to as "the N-methylideneamine oligomer (II)") or a mixture of two or more such oligomers, and a step (hereafter referred to as "step (2)") of hydrolyzing the N-methylideneamine oligomer (II) or the mixture of two or more N-methylideneamine oligomers (II) in the presence of an acid.

Step (1)

In step (1), the ammonium salt compound (I) is reacted with a base, yielding the N-methylideneamine oligomer (II) or a mixture of two or more such oligomers.

In formula (I), A represents an organic group that is either a hydrocarbon group or a heterocyclic group, or said organic group that has a substituent.

Specific examples of the hydrocarbon group include aromatic hydrocarbon groups such as a phenyl group, naphthyl goup, indenyl group, pyrenyl group, acenaphthenyl group, anthxyl group or phenanthryl group, aliphatic hydrocarbon goups such as a methyl group, ethyl group, n-propyl group, isopropyl group, n-butyl group, isobutyl group, s-butyl group, t-butyl group, n-hexyl group, n-octyl group, vinyl group, allyl group, ethynyl group or propargyl group, and alicyclic hydrocarbon groups such as a cyclopropyl group, cyclohexyl group or bicyclo[3.2.1]octyl group. Examples of the heterocyclic group include 5- to 7-membered rings containing 1 to 5 hetero atoms such as an oxygen atom, sulfur atom or nitrogen atom, and condensed rings thereof, and more specific examples include unsaturated 5-membered heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isooxazol-3-yl group, isooxazol-4-yl group, isooxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group, 1,2,4-triazol-5-yl group, 5-phenyl-5-trifluoromethyl-isooxazolin-3-yl group, 2-furfurylmethyl group, 3-thienylmethyl group, or 1-methyl-3-pyrazolomethyl group; unsaturated 6-membered heterocyclic groups such as a pyridin-2-yl group, pyridin-3-yl group, pyridin-4-yl group, pyridazin-3-yl group, pyridazin-4-yl group, pyrazin-2-yl group, pyrimidin-2-yl group, pyrimidin-4-yl group, pyrimidin-5-yl group, 1,3,5-triazin-2-yl group, 1,2,4-triazin-3-yl group, 2-pyridylmethyl group, 3-pyridylmethyl group, 6-chloro-3-pyridylmethyl group or 2-pyrimidylmethyl group; and saturated heterocyclic groups such as a tetrahydrofuran-2-yl group, tetrahydropyran-4-yl group, piperidin-3-yl group, pyrrolidin-2-yl group, morpholino group, piperidino group, N-methylpiperazinyl group, dithianyl group, 2-tetrahydrofuranylmethyl group, 3-piperazinylmethyl group, N-methyl-3-pyrrolidylmethyl group, or motpholinomethyl group. Of these, A is preferably a phenyl group, pyridyl group, thiazolyl group, dithianyl group or tetrahydrofuranyl group.

The hydrocarbon group or heterocyclic group may be substituted, provided the substitution has no effect on the reaction, and specific examples of the substituent include a hydroxyl group; a thiol group; halogen atoms such as a fluorine atom, chlorine atom, bromine atom or iodine atom; a cyano group; a nitro group; a formyl group; unsubstituted or substituted amino groups such as an amino group, methylamino group, benzylamino group, anilino group, dimethylamino group, diethylamino group or phenylethylamino group; alkyl groups (and preferably $C_1$ to $C_6$ alkyl groups) such as a methyl group, ethyl group, n-propyl group, isopropyl group, n-butyl group, sec-butyl group, isobutyl group, t-butyl group, n-pentyl group or n-hexyl group; alkenyl groups such as a vinyl group, allyl group or 2-methoxyethenyl group; alkynyl groups such as an ethynyl group, 1-propynyl group, 2-phenylethynyl group or propargyl group; alkoxy groups (and preferably $C_1$ to $C_6$ alkoxy groups) such as a methoxy group, ethoxy group, propoxy group, isopropoxy group, n-butoxy group, sec-butoxy group, isobutoxy group or t-butoxy group; alkenyloxy groups such as a vinyloxy group or allyloxy group; alkynyloxy groups such as an ethynyloxy group or propargyloxy group; aryloxy groups such as a phenoxy group, benzyloxy group or 2-pyridyloxy group; haloalkyl groups (and preferably $C_1$ to $C_6$ haloalkyl groups) such as a chloromethyl group, fluoromethyl group, bromomethyl group, dichloromethyl group, difluoromethyl group, dibromomethyl group, trichloromethyl group, trifluoromethyl group, bromodifluoromethyl group, trifluoroethyl group, 1-chloroethyl group, 2-chloroethyl group, 1-bromoethyl group, 2-bromoethyl group, pentafluoroethyl group; haloalkoxy groups (and preferably $C_1$ to $C_6$ haloalkoxy groups) such as a fluoromethoxy group, chloromethoxy group, bromomethoxy group, difluoromethoxy group, dichloromethoxy group, dibromomethoxy group, trifluoromethoxy group, trichloromethoxy group, tribromomethoxy group, trifluoroethoxy group, pentafluoroethoxy group or pentafluoropropoxy group; alkylthiocarbonyl groups (and preferably $C_1$ to $C_6$ alkylthiocarbonyl groups) such as a methylthiocarbonyl group, ethylthiocarbonyl group, propylthiocarbonyl group, isopropylthiocarbonyl group, butylthiocarbonyl group, isobutylthiocarbonyl group, sec-butylthiocarbonyl group or t-butylthiocarbonyl group; alkylsulfonylamino groups (and preferably $C_1$ to $C_6$ alkylsulfonylamino groups) such as a methylsulfonylamino group, ethylsulfonylamino group, propylsulfonylamino group, isopropylsulfonylamino group, butylsulfonylamino group or t-butylsulfonylamino group; arylsulfonylamino groups (and preferably $C_6$ to $C_{12}$ arylsulfonylamino groups) such as a phenylsulfonylamino group or piperazinylsulfonylamino group, alkylcarbonylamino groups (and preferably $C_1$ to $C_6$ alkylcarbonylamino groups) such as a methylcarbonylamino group, ethylcarbonylamino group, propylcarbonylamino group or isopropylcarbonylamino group; alkoxycarbonylamino groups (and preferably $C_1$ to $C_6$ alkoxcycarbonylamino groups) such as a methoxycarbonylamino group, ethoxycarbonylamino group, propoxycarbonylamino group or isopropoxycarbonylamino group; haloalkylsulfonylamino groups (and preferably $C_1$ to $C_6$ haloalkylsulfonylamino groups) such as a fluoromethylsulfonylamino group, chloromethylsulfonylamino group, bromomethylsulfonylamino group, difluoromethylsulfonylamino group, dichloromethylsulfonylamino group, difluoromethylsulfonylamino group, trifluoromethylsulfonylamino group, trifluoroethylsulfonylamino group or pentafluoroethylsulfonylamino group; bis(alkylsulfonyl)amino groups (and preferably bis($C_1$ to $C_6$ alkylsulfonyl)amino groups) such as a bis(methylsulfonyl)amino group, bis(ethylsulfonyl)amino group, (methylsulfonyl)(ethylsulfonyl)amino group, bis(propylsulfonyl)amino group, bis(isopropylsulfonyl)amino group, bis(butylsulfonyl)amino group or bis(t-butylsulfonyl)amino group; bis(haloalkylsulfonyl)amino groups (and preferably bis($C_1$ to $C_6$ haloalkylsulfonyl)amino groups) such as a bis(fluoromethylsulfonyl)amino group, bis(chloromethylsulfonyl)amino group, bis(bromomethylsulfonyl)amino group, bis(difluoromethylsulfonyl)amino group, bis(dichloromethylsulfonyl)amino group, bis(difluoromethylsulfonyl)amino group, bis (trifluoromethylsulfonyl)amino group; bis(trifluoroethylsulfonyl)amino group or bis(pentafluoroethylsulfonyl)amino group; unsubstituted or substituted hydrazino groups such as a hydrazino group, N'-phenylhydrazino group or N'-methoxycarbonylhydrazino group; alkoxycarbonyl groups (and preferably $C_1$ to $C_6$ alkoxycarbonyl groups) such as a methoxycarbonyl group, ethoxycarbonyl group, propoxycarbonyl group, isopropoxycarbonyl group, butoxycarbonyl group or t-butoxycarbonyl group; aryl groups (and preferably $C_6$ to $C_{12}$ aryl groups) such as a phenyl group, 1-naphthyl group or 2-naphthyl group; unsaturated 5-membered heterocyclic groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isooxazol-3-yl group, isooxazol-4-yl group, isooxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4,triazol-3-yl group, 1,2,4-triazol-5-yl group, 5-phenyl-5-trifluoromethyl-isooxazolin-3-yl group, 2-furfurylmethyl group, 3-thienylmethyl group or 1-methyl-3-pyrazolomethyl group; unsaturated 6-membered heterocyclic groups such as a pyridin-2-yl group, pyridin-3-yl group, pyridin-4-yl group, pyridazin-3-yl group, pyridazin-4-yl group, pyrazin-2-yl group, pyrimidin-2-yl group, pyrimidin-4-yl group, pyrimidin-5-yl group, 1,3,5-triazin-2-yl group, 1,2,4-triazin-3-yl group, 2-pyridylmethyl group, 3-pyridylmethyl group, 6-chloro-3 pyridylmethyl group or 2-pyrimidylmethyl group; saturated heterocyclic groups such as a tetrahydrofuran-2-yl group, tetrahydrofuran-4-yl group, piperidin-3-yl group, pyrrolidin-2-yl group, morpholino group, piperidino group, N-methylpiperazinyl group, 2-tetrahydrofuranylmethyl group, 3-piperazinylmethyl group, N-methyl-3-pyrrolidylmethyl group or morpholinomethyl group; N-unsubstituted or N-substituted iminoalkyl groups such as an N-dimethylaminoiminomethyl group, 1-N-phenyliminoethyl group, N-hydroxyiminomethyl group or N-methoxyiminomethyl group; N-unsubstituted or N-substituted hydrazinocarbonyl groups such as an N'-methylhydrazinocarbonyl group, N'-phenylhydrazinocarbonyl group or hydrazinocarbonyl group; N-unsubstituted or N-substituted aminocarbonyl groups such as an aminocarbonyl group, dimethylaminocarbonyl group or N-phenyl-N-methylaminocarbonyl group; N-unsubstituted or N-substituted hydrazino groups such as a hydrazino group, N'-acetylhydrazino group, N'-methylhydrazino group, N' phenylhydrazino group or N'-methoxycarbonylhydrazino group; alkylthio groups such as a methylthio group, ethylthio group or t-butylthio group; alkenylthio groups such as a vinylthio group or allylthio group; alkynylthio groups such as an ethynylthio group or propargylthio group; arylthio groups such as a phenylthio group, 4-chlorophenylthio group, benzylthio group, phenethylthio group or 2-pyridylthio group; alkylsulfonyl groups such as a methylsulfonyl group, ethylsulfonyl group or t-butylsulfonyl group; alkenylsulfonyl groups such as an allylsulfonyl group; alkynylsulfonyl groups such as a propargylsulfonyl group; and arylsulfonyl groups such as a phenylsulfonyl group, benzylsulfonyl group or 2-pyridylsulfonyl group. Other novel substituents generated by substituting one substituent with another substituent, thereby combining two or more substituents, may also be used.

More specifically, A is preferably one group selected from the group consisting of groups represented by formulas (IV) to (X), and is most preferably a 2-chloropyridin-5-yl group. Specific examples of X within formulas (IV) to (X) include a hydrogen atom, halogen atoms such as a fluorine atom, bromine atom, chlorine atom or iodine atom, and alkyl groups such as a methyl group, ethyl group, n-propyl group, isopropyl group, n-butyl group, isobutyl group, s-butyl group, t-butyl group, n-hexyl group or n-octylgroup. The alkyl group may include a substituent on an appropriate carbon atom, and examples of the substituent include the same substituents as those exemplified above for A. The substituent within A may be protected with an appropriate protective group prior to conducting the reaction with the base.

In formula (I), specific examples of R include the same groups as those exemplified above for A.

Specific examples of L in formula (I) include a hydrogen atom, halogen atoms such as a fluorine atom, chlorine atom or bromine atom, alkylsulfonyloxy groups of 1 to 20 carbon atoms such as a methylsulfonyloxy group, ethylsulfonyloxy group or n-propylsulfonyloxy group, haloalkylsulfonyloxy groups of 1 to 20 carbon atoms such as a trifluoromethylsulfonyloxy group, trichloromethylsulfonyloxy group, 2,2,2-trifluoroethylsulfonyloxy group or perfluoroethylsulfonyloxy group, and arylsulfonyloxy groups such as a phenylsulfonyloxy group, naphthylsulfonyloxy group, anthrylsulfonyloxy group or phenanthrylsulfonyloxy group. The arylsulfonyloxy groups may include a substituent at an appropriate position, and examples of the substituent include the same substituents as those exemplified above for A. Examples of preferred substituents include halogen atoms such as a fluorine atom, chlorine atom or bromine atom, alkyl groups such as a methyl group or ethyl group, alkoxy groups such as a methoxy group or ethoxy group, haloalkyl groups such as a trifluoromethyl group, and a nitro group.

Although there are no particular restrictions on the process used for producing the ammonium salt compound (I), one example of a preferred process involves reacting a substituted methyl compound represented by formula (XI) (hereafter also referred to as "the substituted methyl compound (XI)"), with either hexamethylenetetramine, or a mixture of ammonia or an ammonium salt and formaldehyde or a formaldehyde equivalent.

The substituted methyl compound (XI) can be produced using conventional methods, and in the case of a compound where A is represented by formula (IV) and X is a halogen atom, can be produced by a process that involves halogenating a 2-halogeno-5-methylpyridine, or a process that involves reacting a 2-halogeno-5-hydroxymethylpyridine with an alkylsulfonyl halide or arylsulfonyl halide in the presence of a base.

Specific examples of the compound represented by formula (XI) include 3-(fluoromethyl)pridine, 3-(chloromethyl)pyridine, 3-(bromomethyl)pyridine, [(pyridin-3-yl)methyl] methyl sulfonate, [(pyridin-3-yl)ethyl]ethyl sulfonate, [(pyridin-3-yl)methyl]-n-propyl sulfonate, [(pyridin-3-yl) methyl]phenyl sulfonate, 2-fluoro-5-(fluoromethyl)pyridine, 5-chloromethyl-2-fluoropyridine, 5-bromomethyl-2-fluoropyridine, [(2-fluoropyridin-5-yl)methyl]methyl sulfonate, [(2-fluoropyridin-5-yl)methyl]ethyl sulfonate, (2-fluoropyridin-5-yl)-n-propyl sulfonate, [(2-fluoropyridin-5-yl)methyl] phenyl sulfonate, 2-chloro-5-(fluoromethyl)pyridine, 2-chloro-5-(chloromethyl)pyridine, 5-bromomethyl-2-chloropyridine, [(2-chloropyridin-5-yl)methyl]methyl sulfonate, [(2-chloropyridin-5-yl)methyl]ethyl sulfonate, [(2-chloropyridin-5-yl)methyl]-n-propyl sulfonate, [(2-chloropyridin-5-yl)methyl]phenyl sulfonate, 2-bromo-5-(fluoromethyl)pyridine, 2-bromo-5-(chloromethyl)pyridine, 2-bromo-5-(bromomethyl)pyridine, [(2-bromopyridin-5-yl)methyl]

methyl sulfonate, [(2-bromopyridin-5-yl)methyl]ethyl sulfonate, [(2-bromopyridin-5-yl)methyl]-n-propyl sulfonate and [(2-bromopyridin-5-yl)methyl]phenyl sulfonate. Of these, 2-chloro-5-(chloromethyl)pyridine is particularly desirable.

There are no particular restrictions on the base used in the reaction with the ammonium salt compound represented by formula (I), and specific examples include alkali metal hydroxides such as sodium hydroxide or potassium hydroxide, alkaline earth metal hydroxides such as magnesium hydroxide or calcium hydroxide, carbonates such as sodium carbonate, potassium carbonate, magnesium carbonate or calcium carbonate, metal alkoxides such as sodium methoxide, sodium ethoxide or magnesium methoxide, and organic bases such as triethylamine, diisopropylethylamine, pyridine, 1,4-diazabicyclo[2.2.2]octane or 1,8-diazabicyclo[5.4.0]-7-undecene. Of these, from the viewpoints of production costs and maximizing the yield of the target product, alkali metal hydroxides are preferred, and sodium hydroxide is particularly desirable.

The pH during the reaction of the ammonium salt compound (I) with the base is typically within a range from 9 to 12, and is preferably controlled within a range from 9.5 to 11.5, and more preferably from 10 to 11. By controlling the pH of the reaction system within this range, the N-methylideneamine oligomer (II) can be produced with good yield.

The reaction between the ammonium salt compound (I) and the base is typically conducted within a solvent. There are no particular restrictions on the solvent used, provided it is inert with respect to the reaction. Examples of solvents that may be used include water; alcohol-based solvents such as methanol, ethanol or n-propanol; aliphatic hydrocarbon-based solvents such as n-pentane, n-hexane, n-heptane or n-octane; alicyclic hydrocarbon-based solvents such as cyclopentane or cyclohexane; aromatic hydrocarbon-based solvents such as benzene, toluene, xylene or chlorobenzene; ketone-based solvents such as acetone, methyl ethyl ketone, diethyl ketone, methyl isopropyl ketone, methyl isobutyl ketone or cyclohexanone; ether-based solvents such as diethyl ether, tetrahydrofuran, dioxane or 1,2-dimethoxyethane; and mixtures of two or more of the above solvents. Of the above possibilities, the use of a mixed solvent of water and an aromatic hydrocarbon-based solvent is preferred, and the use of a mixed solvent of water and toluene is particularly desirable.

The reaction temperature for the reaction between the ammonium salt compound (I) and the base is typically within a range from room temperature to the boiling point of the solvent, and is preferably within a range from 40 to 70° C. The reaction time is typically within a range from several minutes to several days, and is preferably within a range from 1 to 10 hours.

Following completion of the reaction, the reaction liquid may be sampled, and the completion of the reaction can be confirmed using conventional analytical techniques such as thin layer chromatography, gas chromatography or high-performance liquid chromatography.

Further, in the present invention, the N-methylideneamine oligomer (II) may also be obtained in a single step by reacting the substituted methyl compound (XI) with hexamethylenetetramine and a base.

In this case also, the pH of the reaction liquid is typically within a range from 9 to 12, and is preferably controlled within a range from 9.5 to 11.5, and more preferably from 10 to 11. By controlling the pH of the reaction system within this range, the N-methylideneamine oligomer (II) can be obtained with good yield.

The amount of hexamethylenetetramine used is typically within a range from 0.1 to 10 mol, and preferably from 0.25 to 2 mol, per 1 mol of the substituted methyl compound (XI).

Moreover, in the present invention, the N-methylideneamine oligomer (II) may also be obtained in a single step by reacting the substituted methyl compound (XI) with ammonia or an ammonium salt, formaldehyde or a formaldehyde equivalent, and a base.

In this case also, the pH of the reaction liquid is typically within a range from 9 to 12, and is preferably controlled within a range from 9.5 to 11.5, and more preferably from 10 to 11. By controlling the pH of the reaction system within this range, the N-methylideneamine oligomer (II) can be obtained with good yield.

Because this process replaces hexamethylenetetramine with ammonia or an ammonium salt and formaldehyde or a formaldehyde equivalent, all of which are low-cost industrial raw materials, it is particularly advantageous in the case of mass production on an industrial scale.

There are no particular restrictions on the ammonia used, and gaseous ammonia or an aqueous solution or alcohol solution or the like of ammonia may be used. In those cases where an ammonia aqueous solution is used, the concentration of the solution is typically within a range from 5 to 25%, and is preferably from 10 to 25%. Further, an ammonium salt may be used instead of the ammonia. Examples of ammonium salts that may be used include ammonium acetate, ammonium nitrate, ammonium sulfate or ammonium chloride.

The amount of ammonia used is typically within a range from 1 to 40 mol, and preferably from 1 to 8 mol, per 1 mol of the substituted methyl compound (XI).

There are no particular restrictions on the formaldehyde used, and an aqueous solution or alcohol solution or the like of formaldehyde may be used. Furthermore, a formaldehyde equivalent may also be used instead of formaldehyde. An example of the formaldehyde equivalent is paraformaldehyde, which is a polymer of formaldehyde. Paraformaldehyde is a white powder at room temperature, and can be used to generate formaldehyde by dissolution in the organic solvent and subsequent heating.

The amount of formaldehyde used is typically within a range from 0.1 to 20 mol, and preferably from 1 to 2 mol, per 1 mol of ammonia.

In the cases described above, the substituted methyl compound (XI) is reacted with the hexamethylenetetramine, or with the ammonia or the like and formaldehyde or the like, and the hexamethylenetetramine or the ammonia and the formaldehyde can be recovered from the obtained reaction mixture and subsequently reused in reaction with the substituted methyl compound (XI). By recovering the hexamethylenetetramine or the ammonia and the formaldehyde for reuse in the reaction with the substituted methyl compound (XI), the overall amounts used of the hexamethylenetetramine or the ammonia and formaldehyde can be reduced, enabling the N-methylideneamine oligomer (II) to be produced at lower cost.

Furthermore, in those cases where the solution containing the recovered ammonia and formaldehyde is used in a continuous process, the solution may be used as is, although in those cases where the ratio of ammonia and formaldehyde within the recovered solution differs from the ratio required to ensure continuity of the reaction, a supplementary amount of the component among the ammonia and the aldehyde that is lacking must be added to the solution. In other words, if the amount of ammonia is insufficient, then ammonia or an ammonium salt is added, whereas if the amount of the formaldehyde is insufficient, formaldehyde or a formaldehyde equivalent is added, thereby adjusting the ratio between the ammonia and the formaldehyde to the optimum ratio. This optimum ratio varies depending on factors such as the reaction conditions, but the amount of the formaldehyde is typically within a range from 0.1 to 20 mol, and preferably from 1 to 2 mol, per 1 mol of the ammonia.

In those cases where a mixture of the substituted methyl compound (XI) with either hexamethylenetetramine, or ammonia or the like and formaldehyde or the like is used instead of the ammonium salt compound (I), the base and solvent used, and other factors such as the reaction temperature and the like may all be the same as those described above for the reaction that uses the ammonium salt compound (I).

In either case, the N-methylideneamine oligomer (II) or mixture of two or more such oligomers that represents the target product can be isolated using typical post-processing operations.

The structure of the obtained N-methylideneamine oligomer (II) can be confirmed using conventional analytical techniques such as $^1$H-NMR, $^{13}$C-NMR, IR spectroscopy, mass spectrometry and elemental analysis.

The structure of the N-methylideneamine oligomer (II) may be a chain-like structure, a cyclic structure, or a structure containing both chain-like and cyclic portions, although a cyclic compound represented by formula (II') is particularly desirable. In formula (II'), X is as defined above, and examples thereof include the same substituents as those exemplified above. In either formula (II) or formula (II'), n represents an integer of 2 to 20, and is preferably within a range from 2 to 10, and more preferably from 2 to 5. Based on the various spectra mentioned above, the N-methylideneamine oligomer (II) is thought to have a structure such as those shown below.

[Chemical Formula 11]

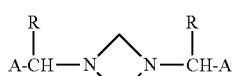
(II-a)

[Chemical Formula 12]

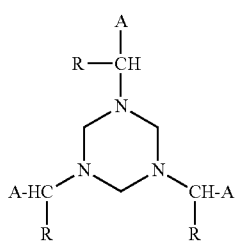
(II-b)

[Chemical Formula 13]

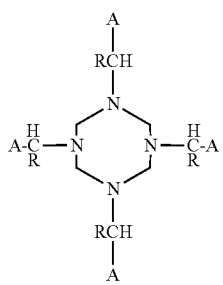
(II-c)

Triazine derivatives represented by formula (II') are particularly desirable.

The N-methylideneamine oligomer (II) or the mixture of two or more such oligomers obtained in the manner described above is useful as an intermediate for the production of the amine compound (III).

In the present invention, following completion of the reaction, the imine compound (II) or the mixture of two or more such compounds need not necessarily be isolated from the reaction solution, and the reaction solution may be supplied, as is, to the subsequent step (2).

In other words, the N-methylideneamine oligomer (II) is a basic substance, and has the property of being soluble in acidic water. Accordingly, by conducting the reaction between the ammonium salt compound (I) and the base in a mixed solvent medium containing water and an organic solvent that is immiscible with water, such as a mixed solvent medium composed of water and toluene, subsequently separating the organic layer from the obtained reaction mixture, and then extracting the separated organic layer with acidic water, a salt of the N-methylideneamine oligomer (II) or mixture of two or more such oligomers that represents the target product can be obtained as an aqueous solution. This aqueous solution may be supplied, as is, to the subsequent step (2).

Step (2)

Step (2) involves hydrolyzing the N-methylideneamine oligomer (II) or the mixture of two or more such oligomers in the presence of an acid to obtain the amine compound (III).

There are no particular restrictions on the acid used in the reaction, and specific examples include inorganic acids such as sulfuric acid, hydrochloric acid or phosphoric acid, organic carboxylic acids such as acetic acid or trifluoroacetic acid, organic sulfonic acids such as p-toluenesulfonic acid, methanesulfonic acid or trifluoromethanesulfonic acid, and Lewis acids such as boron trifluoride, titanium tetrachloride or aluminum chloride.

The amount of acid used is typically within a range from 1 to 100 mol, preferably from 2 to 20 mol, and more preferably from 3 to 10 mol, per 1 mol of the ammonium salt compound (I) or the substituted methyl compound (XI). By setting the amount of acid used to a value within this range, the targeted substituted methylamine compound (III) can be obtained with good yield.

The hydrolysis reaction of the N-methylideneamine oligomer (II) or mixture of two or more such oligomers in the presence of an acid is typically conducted with the reactants diluted with a solvent. Examples of this solvent include the same solvents as those exemplified above for use within the reaction of the substituted methyl compound (XI) with hexamethylenetetramine, or the mixture of ammonia or the like and formaldehyde or the like. Of these solvents, a mixed solvent containing water and an alcohol is preferred, and a mixed solvent containing water and methanol is particularly desirable.

The reaction temperature during the hydrolysis of the N-methylideneamine oligomer (II) or mixture of two or more such oligomers in the presence of an acid is typically within a range from room temperature to 90° C., and is preferably from 50 to 90° C. The reaction time is typically within a range from several minutes to several days, and is preferably within a range from 1 to 10 hours. Following completion of the reaction, the reaction liquid may be sampled, and the completion of the reaction can be confirmed using conventional analytical techniques such as thin layer chromatography, gas chromatography or high-performance liquid chromatography.

Following completion of the reaction, the target amine compound (III) can be obtained by conducting typical post-processing operations, and then using conventional purification techniques such as distillation and column chromatography.

According to the present invention, the amine compound (III), and preferably a pyridylmethylamine compound represented by formula (III'):

[Chemical Formula 14]

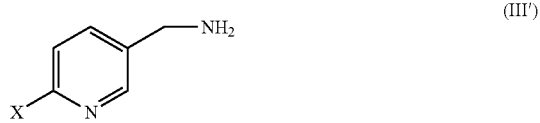

(III')

(wherein X is as defined above)
can be produced easily, with good yield, and at low cost.

The amine compound (III) obtained using the production process of the present invention is useful as an intermediate in the production of agricultural chemicals and medicines and the like, such as an intermediate in the production of the active component in chloronicotinyl-based agricultural and horticultural insecticides such as imidacloprid, nitenpyram and acetamiprid.

Furthermore, according to the production process of the present invention, by reacting a hexamethylenetetraammonium salt compound represented by formula (XII):

[Chemical Formula 15]

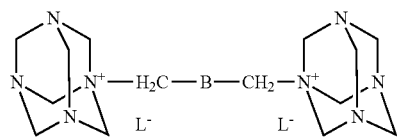

(XII)

(wherein B represents a phenyl group, pyridyl group, thiazolyl group, dithianyl group or tetrahydrofuranyl group, and most preferably represents a dithianyl group, and L is as defined above)
with a base, an N-methylideneamine oligomer represented by formula (XIII):

[Chemical Formula 16]

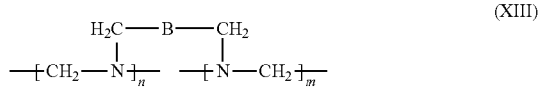

(XIII)

(wherein B is as defined above, and n and m each independently represents an integer of 2 to 20) or a mixture of two or more such oligomers can be obtained, and by subsequently hydrolyzing the N-methylideneamine oligomer represented by formula (XIII) or the mixture of two or more such oligomers in the presence of an acid, a substituted methylamine compound represented by formula (XIV) can be produced.

[Chemical Formula 17]

$$H_2N-H_2C-B-CH_2-NH_2 \qquad (XIV)$$

(wherein B is as defined above.)

Furthermore, according to the production process of the present invention, by reacting a substituted methyl compound represented by formula (XV):

[Chemical Formula 18]

$$L-H_2C-B-CH_2-L \qquad (XV)$$

(wherein B and L are as defined above)
with hexamethylenetetramine, or ammonia or an ammonium salt and formaldehyde or a formaldehyde equivalent, and a base, an N-methylideneamine oligomer represented by formula (XIII) or a mixture of two or more such oligomers can be obtained, and by subsequently hydrolyzing the N-methylideneamine oligomer represented by formula (XIII) or the mixture of two or more such oligomers in the presence of an acid, a substituted methylamine compound represented by formula (XIV) can be produced.

In this manner, the production process of the present invention enables even compounds that have proven impossible to produce with conventional processes to be produced easily, with good yield, and at low cost.

EXAMPLES

The present invention is described in further detail below using a series of examples, although the present invention is in no way limited by these examples.

Analysis of the reaction products was performed using high-performance liquid chromatography (HPLC, model LC-10, manufactured by Shimadzu Corporation) and gas chromatography (GC, model GC-14B, manufactured by Shimadzu Corporation).

Example 1

Production of (2-chloropyridin-5-yl)methylamine (1)

To 3.02 g (10 mmol) of (2-chloropyridin-5-yl)hexamethylenetetraammonium chloride (I-1) were added 5 ml of water and 5 ml of toluene, and the resulting mixture was stirred for 7 hours at 60° C. while a 28% aqueous solution of sodium hydroxide was used to maintain the pH of the reaction mixture within a range from 10 to 11.

An additional 4 ml of toluene was added to the reaction mixture, and the toluene layer was separated. 7 g of concentrated hydrochloric acid was added to the toluene layer, and the water layer containing the hydrochloride salt of an N-methylidene-2-chloro-3-pyridylmethylamine oligomer (II-1) or a mixture of two or more such salts was separated.

3.2 g of methanol was added to the separated water layer, and the resulting mixture was treated for 3 hours at 60° C., yielding an aqueous solution of the hydrochloride salt of (2-chloropyridin-5-yl)methylamine (III-1). Analysis by HPLC revealed a product amount of 1.21 g (yield: 85%).

Example 2

Production of (2-chloropyridin-5-yl)methylamine (2)

To 1.62 g (10 mmol) of 2-chloro-5-(chloromethyl)pyridine (XI-1) and 1.48 g (10 mmol) of hexamethylenetetramine were added 5 ml of water and 1 ml of toluene, and the resulting mixture was stirred for 7 hours at 60° C. while a 28% aqueous solution of sodium hydroxide was used to maintain the pH of the reaction mixture within a range from 10 to 11.

An additional 4 ml of toluene was added to the reaction mixture, and the toluene layer was separated. 7 g of concentrated hydrochloric acid was added to the toluene layer, and the water layer containing the hydrochloride salt of an N-methylidene-2-chloro-3-pyridylmethylamine oligomer (II-1) or a mixture of two or more such salts was separated.

3.2 g of methanol was added to the separated water layer, and the resulting mixture was treated for 3 hours at 60° C., yielding an aqueous solution of the hydrochloride salt of (2-chloropyridin-5-yl)methylamine (III-1). Analysis by HPLC revealed a product amount of 1.28 g (yield: 90%).

Example 3

Production of (2-chloropyridin-5-yl)methylamine (3)

To 1.62 g (10 mmol) of 2-chloro-5-chloromethylpyridine (XI-1) and 0.7 g (5 mmol) of hexamethylenetetramine were added 5 ml of water and 1 ml of toluene, and the resulting mixture was stirred for 7 hours at 60° C. while a 28% aqueous solution of sodium hydroxide was used to maintain the pH of the reaction mixture within a range from 10 to 11.

An additional 4 ml of toluene was added to the reaction mixture, and the toluene layer was separated. 7 g of concentrated hydrochloric acid was added to the toluene layer, and the water layer containing the hydrochloride salt of a pyridylmethylimine compound (II-3) or a mixture of two or more such salts was separated.

3.2 g of methanol was added to the separated water layer, and the resulting mixture was treated for 3 hours at 60° C., yielding an aqueous solution of the hydrochloride salt of (2-chloropyridin-5-yl)methyl amine (III-1). Analysis by HPLC revealed a product amount of 1.26 g (yield: 89%).

Comparison with example 2 above confirmed that even if the amount of hexamethylenetetramine was reduced, there was no substantial effect on the yield of the target product.

Example 4

Production of 1,3,5-tris[(2-chloropyridin-5-yl)methyl]-1,3,5-perhydrotriazine

To a mixed solution containing 10 ml of methanol and 10 ml of water were sequentially added 2.72 g (40 mmol) of a 25% aqueous solution of ammonia, 1.21 g (40 mmol) of paraformaldehyde, and 3.24 g (20 mmol) of 2-chloro-5-(chloromethyl)pyridine (XI-1), and the resulting mixture was stirred for 2.5 hours at 50° C. while a 28% aqueous solution of sodium hydroxide was used to maintain the pH of the reaction mixture within a range from 10 to 11. The reaction mixture was then extracted with chloroform, and the chloroform layer was separated and concentrated, yielding 2.50 g (yield: 81%) of 1,3,5-tris(2-chloropyridin-5-yl)methyl-1,3,5-perhydrotriazine (II-4).

$^1$H-NMR (CDCl$_3$, δ ppm): 3.37 (bs, 6H), 3.62 (s, 6H), 7.26 (d, 3H), 7.61 (d, 3H), 8.33 (s, 3H)

m/s: 462

Example 5

Production of (2-chloropyridin-5-yl)methylamine (4)

To 0.77 g (1.66 mol) of 1,3,5-tris[(2-chloropyridin-5-yl)methyl]-1,3,5-perhydrotriazine (II-4) were sequentially added 0.40 g of methanol and 1.83 g of concentrated hydrochloric acid, and the resulting mixture was stirred at 75 to 80° C. for 6 hours. The reaction mixture was then diluted with chloroform, and following conversion of the mixture to an alkaline state by adding a 28% aqueous solution of sodium hydroxide, the chloroform layer was separated and concentrated, yielding 0.68 g (yield: 95%) of (2-chloropyridin-5-yl)methylamine (III-1).

Example 6

Production of (2-chloropyridin-5-yl)methylamine (5)

To 1.62 g (10 mmol) of 2-chloro-5-(chloromethyl)pyridine (XI-1) and 1.48 g (10 mmol) of hexamethylenetetramine were added 5 ml of water and 1 ml of toluene, and the resulting mixture was stirred for 7 hours at 60° C. while a 28% aqueous solution of sodium hydroxide was used to maintain the pH of the reaction mixture within a range from 10 to 11. An additional 4 ml of toluene was then added to the reaction mixture, and the water layer was separated to recover the hexamethylenetetramine. Analysis by GC revealed a recovery rate of 73%.

The toluene layer was treated in the same manner as example 2, yielding (2-chloropyridin-5-yl)methylamine (III-1).

To the aqueous solution containing hexamethylenetetramine recovered in the manner described above were added 1.62 g (10 mmol) of 2-chloro-5-(chloromethyl)pyridine (XI-1), 0.52 g (3.5 mmol) of hexamethylenetetramine, 0.18 g of ammonium chloride and 1 ml of toluene, and the resulting mixture was heated for 7 hours at 60° C. while a 28% aqueous solution of sodium hydroxide was used to maintain the pH of the reaction mixture within a range from 10 to 11. An additional 4 ml of toluene was then added to the reaction mixture, and the toluene layer and water layer were each separated. The hexamethylenetetramine was recovered from the water layer, and the recovery rate was 69%.

On the other hand, 7 g of concentrated hydrochloric acid was added to the toluene layer, and the resulting water layer containing the hydrochloride salt of an N-methylidene-(2-chloro-pyridin-5-yl)methylamine oligomer (II-5) or a mixture of two or more such salts was separated. 3.2 g of methanol was added to the separated water layer, and the resulting mixture was treated for 3 hours at 60° C., yielding an aqueous solution of the hydrochloride salt of (2-chloropyridin-5-yl)methylamine. Analysis by HPLC revealed an amount of the (2-chloropyridin-5-yl)methylamine of 1.28 g (yield: 90%).

As described above, in the examples, approximately 70% of the hexamethylenetetramine was able to be recovered, and by simply supplementing the reaction with the required amount of additional hexamethylenetetramine, the reaction was able to be continued at the same scale.

The invention claimed is:

1. A process for producing an N-methylidene-substituted methylamine oligomer or a mixture of two or more of the oligomers, said process comprising:

reacting a hexamethylenetetraammonium salt compound represented by a formula (I) shown below:

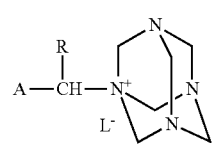

wherein A represents an organic group that is either a hydrocarbon group or a heterocyclic group, or said organic group that has a substituent, R represents a hydrogen atom, an organic group that is either a hydrocarbon group or a heterocyclic group, or said organic group that has a substituent, and L represents a halogen atom, an alkylsulfonyloxy group of 1 to 20 carbon atoms, a haloalkylsulfonyloxy group of 1 to 20 carbon atoms, or a substituted or unsubstituted arylsulfonyloxy group with a base to obtain an N-methylidene-substituted methylamine oligomer represented by a formula (II) shown below:

$$A-CH-R \\ -\!\!\!+\!\!N-CH_2\!\!+\!\!-_n$$ (II)

wherein A and R are as defined above, and n represents an integer of 2 to 20 or a mixture of two or more of the oligomers, wherein reaction between said hexamethylenetetraammonium salt compound represented by said formula (I) and said base is conducted at a pH of 10.0 to 11.5.

2. The process for producing an N-methylidene-substituted methylamine oligomer or a mixture of two or more of the oligomers according to claim 1, wherein said A represents an organic group selected from the group consisting of -a phenyl group, a pyridyl group, a thiazolyl group, a dithianyl group and a tetrahydrofuranyl group, and said organic group having a substituent.

3. The process for producing an N-methylidene-substituted methylamine oligomer or a mixture of two or more of the oligomers according to claim 2, wherein said A represents one group selected from the group consisting of groups represented by formulas (IV) to (X) shown below:

(IV)

(V)

(VI)

(VII)

(VIII)

(IX)

(X)

wherein X represents a hydrogen atom, a halogen atom, or a substituted or unsubstituted alkyl group.

4. The process for producing an N-methylidene-substituted methylamine oligomer or a mixture of two or more of the oligomers according to claim 3, wherein said A is a 2-chloropyridin-5-yl group.

5. The process for producing an N-methylidene-substituted methylamine oligomer or a mixture of two or more of the oligomers according to claim 1, wherein said R represents a hydrogen atom or an alkyl group of 1 to 5 carbon atoms.

6. A process for producing an N-methylidene-substituted methylamine oligomer or a mixture of two or more of the oligomers, said process comprising:

reacting a substituted methyl compound represented by a formula (XI) shown below:

$$A-\underset{\underset{L}{|}}{\overset{\overset{R}{|}}{CH}}$$ (XI)

wherein A represents an organic group that is either a hydrocarbon group or a heterocyclic group, or said organic group that has a substituent, R represents a hydrogen atom, an organic group that is either a hydrocarbon group or a heterocyclic group, or said organic group that has a substituent, and L represents a halogen atom, an alkylsulfonyloxy group of 1 to 20 carbon atoms, a haloalkylsulfonyloxy group of 1 to 20 carbon atoms, or a substituted or unsubstituted arylsulfonyloxy group with hexamethylenetetramine, or ammonia or an ammonium salt and formaldehyde or a formaldehyde equivalent, and a base to obtain an N-methylidene-substituted methylamine oligomer represented by a formula (II) shown below:

$$A-CH-R \\ -\!\!\!+\!\!N-CH_2\!\!+\!\!-_n$$ (II)

wherein A and R are as defined above, and n represents an integer of 2 to 20, or a mixture of two or more of the oligomers, wherein reaction of said substituted methyl compound represented by said formula (XI) with hexamethylenetetramine, or ammonia or an ammonium salt and formaldehyde or a formaldehyde equivalent, and a base is conducted at a pH of 10.0 to 11.5.

7. The process for producing an N-methylidene-substituted methylamine oligomer or a mixture of two or more of the oligomers according to claim 6, wherein said A represents an organic group selected from the group consisting a phenyl group, a pyridyl group, a thiazolyl group, a dithianyl group and a tetrahydrofuranyl group, and said organic group having a substituent.

8. The process for producing an N-methylidene-substituted methylamine oligomer or a mixture of two or more of the oligomers according to claim 7, wherein said A represents one group selected from the group consisting of groups represented by formulas (IV) to (X) shown below:

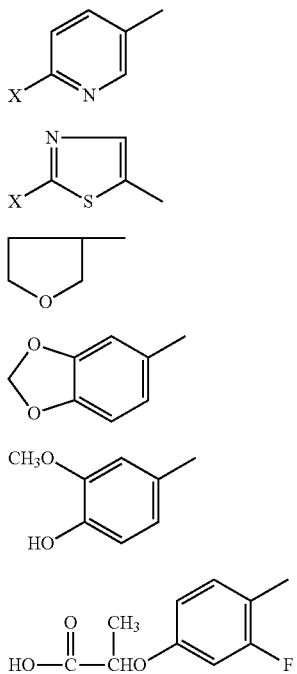

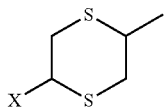

wherein X represents a hydrogen atom, a halogen atom, or a substituted or unsubstituted alkyl group.

9. The process for producing an N-methylidene-substituted methylamine oligomer or a mixture of two or more of the oligomers according to claim 8, wherein said A is a 2-chloropyridin-5-yl group.

10. The process for producing an N-methylidene-substituted methylamine oligomer or a mixture of two or more of the oligomers according to claim 6, wherein said R represents a hydrogen atom or an alkyl group of 1 to 5 carbon atoms.

11. The process for producing an N-methylidene-substituted methylamine oligomer or a mixture of two or more of the oligomers according to claim 6, wherein hexamethylenetetramine, or ammonia and formaldehyde, are recovered from a reaction mixture obtained following reaction of said substituted methyl compound represented by said formula (XI) with hexamethylenetetramine, or ammonia or an ammonium salt and formaldehyde or a formaldehyde equivalent, and are subsequently reused in reaction with said substituted methyl compound represented by said formula (XI).

\* \* \* \* \*